(12) United States Patent
Pan et al.

(10) Patent No.: US 7,150,886 B2
(45) Date of Patent: Dec. 19, 2006

(54) COMPOSITION FOR TREATING DISEASED LIVER

(75) Inventors: I-Horng Pan, Hsinchu (TW); Hsi-Ho Chiou, Hsinchu (TW); Chu-Hsun Lu, Kaohsiung (TW); Chaurp-Ting Ju, Hsinchu (TW); Wei-Lun Fan, Miaoli (TW); Wen-Huang Peng, Changhua (TW); Ming-Tsuen Hsieh, Taichung (TW)

(73) Assignee: Industrial Technology Research Institute (TW)

( * ) Notice: Subject to any disclaimer, the term of this patent is extended or adjusted under 35 U.S.C. 154(b) by 83 days.

(21) Appl. No.: 10/646,793

(22) Filed: Aug. 25, 2003

(65) Prior Publication Data

US 2004/0052876 A1    Mar. 18, 2004

(30) Foreign Application Priority Data

Sep. 13, 2002    (TW) ................................. 91120960

(51) Int. Cl.
*A61K 36/00* (2006.01)

(52) U.S. Cl. ....................................................... 424/725
(58) Field of Classification Search ................ 424/725, 424/195.1
See application file for complete search history.

(56) References Cited

FOREIGN PATENT DOCUMENTS

KR    2001102650 A  * 11/2001
KR    2002090175 A  * 11/2002

* cited by examiner

*Primary Examiner*—Patricia Leith
(74) *Attorney, Agent, or Firm*—Bacon & Thomas, PLLC

(57) ABSTRACT

The present invention relates to a composition for liver protection and a preparing method of the same, the processes are as follows: grinding Artemisiae Capillaris and Gardeniae Fructus, mixing with pure water, and boiling the mixture. Then, adding the Rhei Rhizoma alcohol solution into the mixture for extraction to form the first solid phase and the first liquid phase, further concentrating the first liquid phase to form a concentrate, and adding alcohol into the concentrate for precipitation to form the second solid phase and second liquid phase, and separating the second solid phase and drying.

29 Claims, 5 Drawing Sheets

COMPOSITION FOR TREATING DISEASED LIVER

BACKGROUND OF THE INVENTION

1. Field of the Invention

The present invention relates to a Chinese herb composition and, more particularly, to a Chinese herb composition suitable for treating hepatitis.

2. Description of Related Art

Chronic liver diseases (such as chronic hepatitis, cirrhosis, and liver cancer) have been a major cause of deaths in humans for centuries. The liver diseases include viral liver disease, alcoholic liver disease, drug or toxicant-caused liver disease and metabolism disorder liver disease. In the world, about 350 million people are chronic B type hepatitis carriers, and 2.7 million people are chronic C type hepatitis carriers. In Taiwan, the B type hepatitis carrier rate is about 15 to 20% of the population and the C type hepatitis carrier rate is about 2 to 4% of the population. Therefore, there is a serious demand for effective treatment of these diseases. The present medicines for treating hepatitis, such as liver protecting drugs, antiviral drugs or immune regulators, certainly have curative effects, but they also have side effects and are expensive. For example, the interferon and lamivudineare used for treating B type hepatitis. The interferon, which were approved by the FDA in 1992 for treating B type hepatitis, have only a 20% positive response but also have severe side effects. On the other hand, lamivudine, which was approved by the FDA in 1998 for treating B type hepatitis, also has only a 17 to 33% positive response. Furthermore, Lamivudine™ easily causes the mutation of B type hepatitis virus and thus reduces the potency of the treatment.

In reference to traditional Chinese medicine, hepatitis is usually treated with a prescription of herbs and other natural ingredients, however the potency is too variable and thus unreliable. These shortcomings may be due to a lack of common scientific standards among the practitioners. Thus, there is a long, unfulfilled need for a reliable and inexpensive medication to cure and prevent common liver diseases, and which further is not accompanied by side effects experienced with existing medications for liver ailments. The present invention provides a composition for curing various forms of hepatitis found in a human body, and a novel process of the same.

Traditional Chinese medicines are usually extracted by water decoction, but this method cannot obtain enough active components. In addition, the active components will lose their activity at high decocting temperatures. Many processes for preparing liver protecting drugs have been disclosed in, for example, Patents CN 1194840, CN 1110151, CN 1136941 and CN 119540. However, the prior arts use complex materials and traditional processes, which do not overcome the above problems (i.e. loss of activity). Alternatively, Patents JP 6322116, JP 58183623, U.S. Pat. No. 5,529,778 and U.S. Pat. No. 5,145,955 disclose processes, which utilize organic solvents, such as methanol, acetone and chloroform, to extract the active components. However, these organic solvents are toxic and need to be removed completely, or they will harm human bodies.

Therefore, it is desirable to provide a novel process for preparing the composition for liver protection, and the effective components of said product are higher than those found in existing traditional medicines. There are more active substances and good curative effects, but no toxic organic solvents are involved in the process and thus harmful side effects found in using existing medicines are absent from the present invention.

SUMMARY OF THE INVENTION

The object of the present invention is to provide a composition for treating a diseased liver and for preventing a healthy liver becoming diseased, which further serves as a drug for treating chronic hepatitis.

Another object of the present invention is to provide a process for preparing the composition for treating a diseased liver; said process efficiently extracts the active components from the composition without involving the use of toxic organic solvents.

To achieve the object, the processes for preparing a composition for treating a human liver of the present invention are described below. Artemisiae Capillaris and Gardeniae Fructus are ground, mixed with pure water, and decocted. Then, a Rhei Rhizoma herb and alcohol are added to said mixture for precipitation to form the first solid phase and the first liquid phase, further said both phases are separated, and said first liquid phase is concentrated to form a liquid concentrate. Again, alcohol is subsequently added to said concentrate for precipitation to form the second solid phase and second liquid phase, and said second solid phase is separated and dried.

The present invention further relates to a composition for treating hepatitis, which is prepared by the process mentioned above.

Other objects, advantages, and novel features of the invention will become more apparent from the following detailed description when taken in conjunction with the accompanying drawings.

DETAILED DESCRIPTION OF THE PREFERRED EMBODIMENT

The present invention relates to a composition for treating hepatitis and a preparing method of the same, the processes are as follows: first, Artemisiae Capillaris and Gardeniae Fructus are ground to a powder, mixed with pure water, decocted, and then cooled to form a water extract. Wherein, said decocting step preferably is multiple boilings and stirrings, and said preferable cooling step is cooled at 10 to 80° C. Preferably, said Artemisiae Capillaris is selected from the group consisting of Artemisiae Capillaris, Herba Artemisiae Annuae, Artemisiae Scopariae Herba and the herbs of the same genus. On the other hand, said Gardeniae Fructus is preferably selected from the group consisting of Gardenia Jasminoides, Gardenia Radicans and the herbs of the same genus. Then, the Rhei Rhizoma herb and alcohol are added to said mixture, said preferable extracting temperature is 10 to 80° C. Said Rhei Rhizoma is preferably selected from the group consisting of Rheum Officinalis, Rhubarb Shui-Ken and the herbs of the same genus. At this time, the Schizandrae Fructus herb and alcohol are optionally added. Wherein, said weight ratio of Artemisiae Capillaris to Gardeniae Fructus to Rhei Rhizoma is not limited, and preferably is 4–8 to 3–6 to 0.5–1.5, and more preferably is 4 to 3 to 1, 4 to 3 to 2, 4 to 6 to 1, or 8 to 3 to 2.

A first solid phase and a first liquid phase are formed after extracting, and said two phases are then separated. Further, said first liquid phase is concentrated to form a liquid concentrate; preferably, said liquid concentrate is a concentrate containing 1 to 30 wt % solid. Then, alcohol is added to said concentrate for precipitation to form a second solid phase and a second liquid phase. Preferably, a final concentration of the added alcohol is greater than 30 wt %. This step provides a first way and a second way in respect to conditions of the patient to be treated. The first way is adding alcohol until its final concentration is 71 to 90 wt % to form a second solid phase and a second liquid phase. The second solid phase is dried, and packaged.

The second way is adding alcohol until the final concentration is 30 to 70 wt % to form a second solid phase and a second liquid phase. The second solid phase is then dried and packaged. Due to the lower alcohol concentration used in this step, there are still some active components remaining in the second liquid phase. Hence, alcohol is further added into the residual second liquid phase until its final concentration is from 75 to 90 wt % and a third solid phase and a third liquid phase are formed. The third solid phase is then dried and packaged. The mentioned drying method is not limited, and preferably is lyophilizing, spray drying or fluidized bed drying method. Finally, the product is dried and ground to powder followed by being granulated and packaged as capsules.

A. Preparation of the Extract

Figure 6:
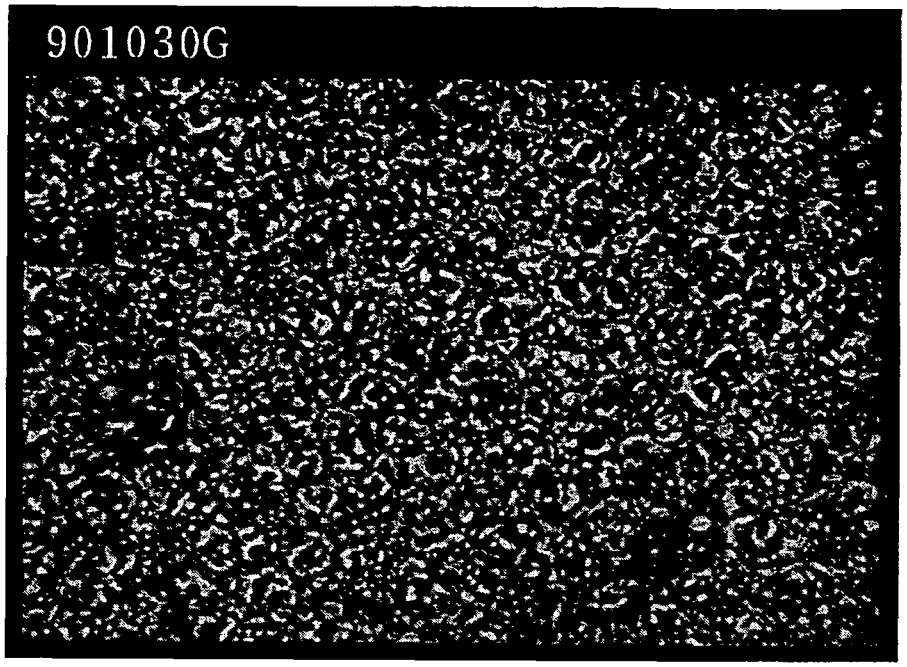
FIG. 6 is a biopsy of a liver with $CCl_4$-induced acute hepatitis and treated with ICH 17 observed through an optical microscope.

Embodiment 1
1. 8 kg of Artemisiae Capillaris, 6 kg of ground Gardenia Jasminoides and 144 kg of pure water are added together into a 250 ml decocting trough, then mixed and soaked for 13 h.
2. Said mixture is extracted at 80° C. for 1 h, and cooled to 35° C. for further use.
3. 2 kg of ground Rheum Officinalis and 48 kg of 95% ethanol are added into the above-mentioned liquid decoction at 35° C. for 1 h for extraction.
4. Said extraction of the liquid decoction is filtrated through a 200-mesh sieve and 168.89 kg of liquid extract is thus obtained, which contains 1.01 wt % solid, measured by a moisture analyzer.
5. Said liquid extract is concentrated under reduced pressure by vacuum concentrator to obtain 16.51 kg of liquid concentrate, containing 10.05 wt % solid measured by moisture analyzer.
6. Said liquid concentrate is put into a precipitating tank and stirred by mechanical mixer. 15.58 kg of 95% ethanol is slowly added until final concentration of the mixed liquid concentrateis about 50%. Then, the mixer is stopped and incubated for 1 h.
7. Said mixture is further filtrated by centrifugation using a centrifugal filtrator, and the filtrate is then collected and dried by a lyophilizer to obtain 65.26 g of product, which is coded as ICH17. An animal study was performed with said product, and the results are shown as Tables 1, 3 and FIG. 6.

Figure 1:
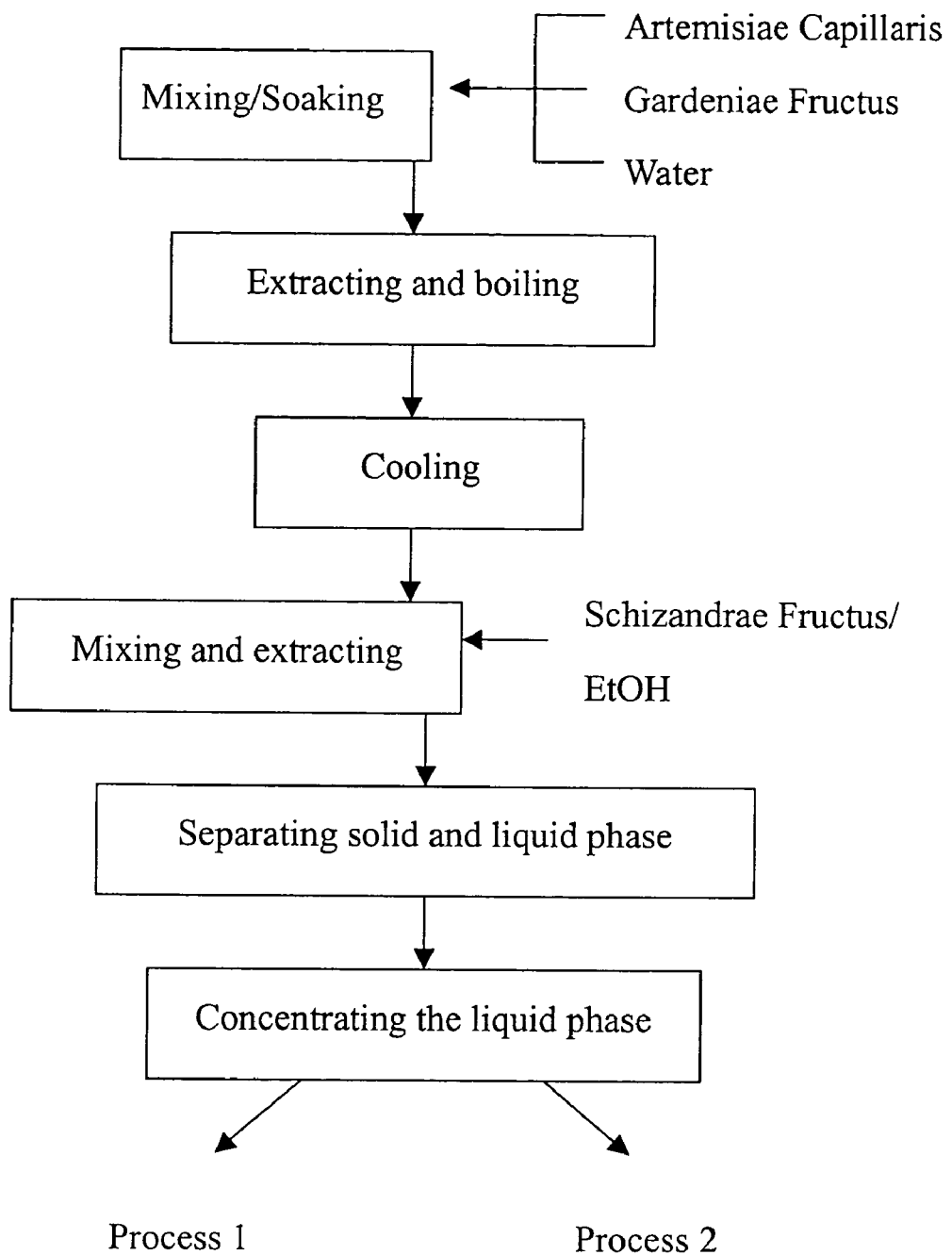
FIG. 1 is an illustration of the preparation process of the present invention.
Figure 1:
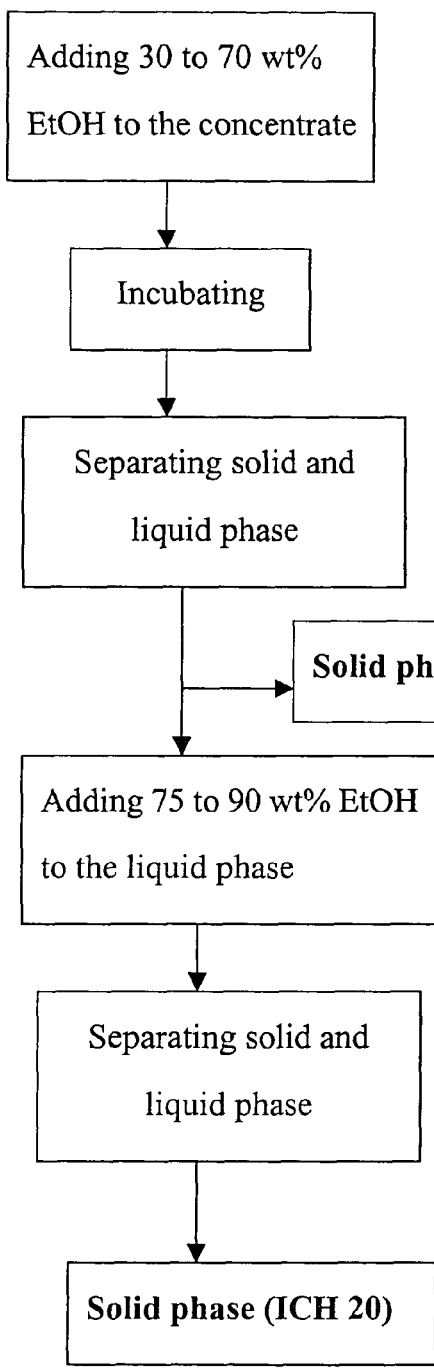
Figure 1:
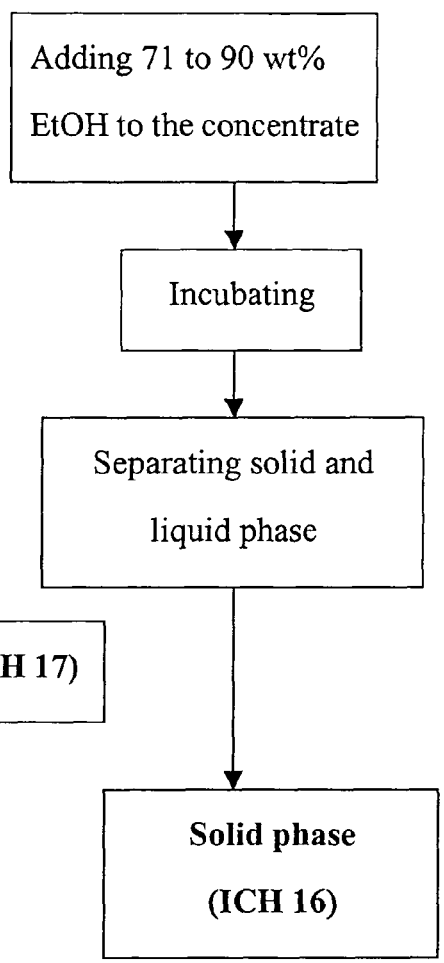
Figure 2:
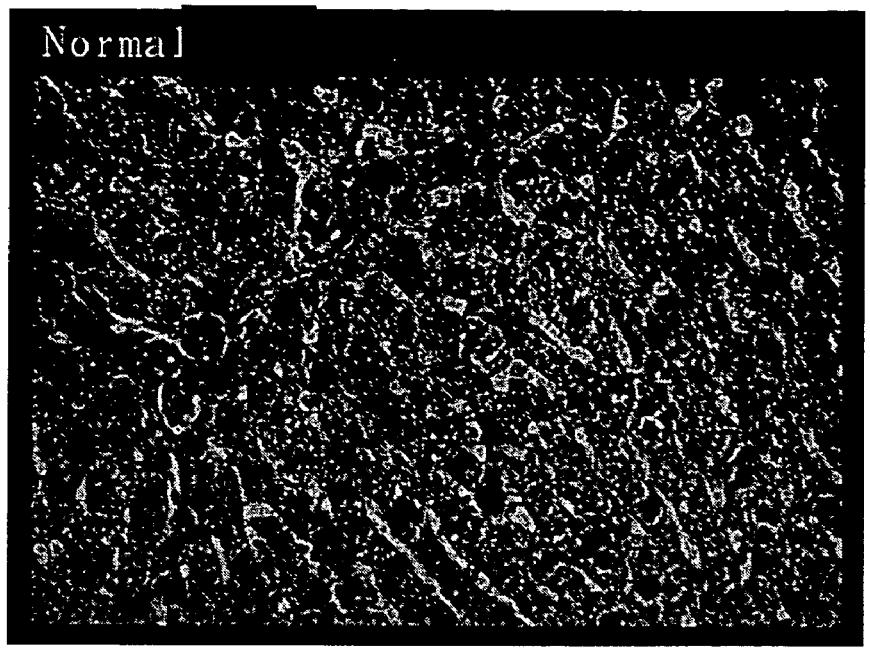
FIG. 2 is a biopsy of a normal liver observed through an optical microscope.
Figure 3:
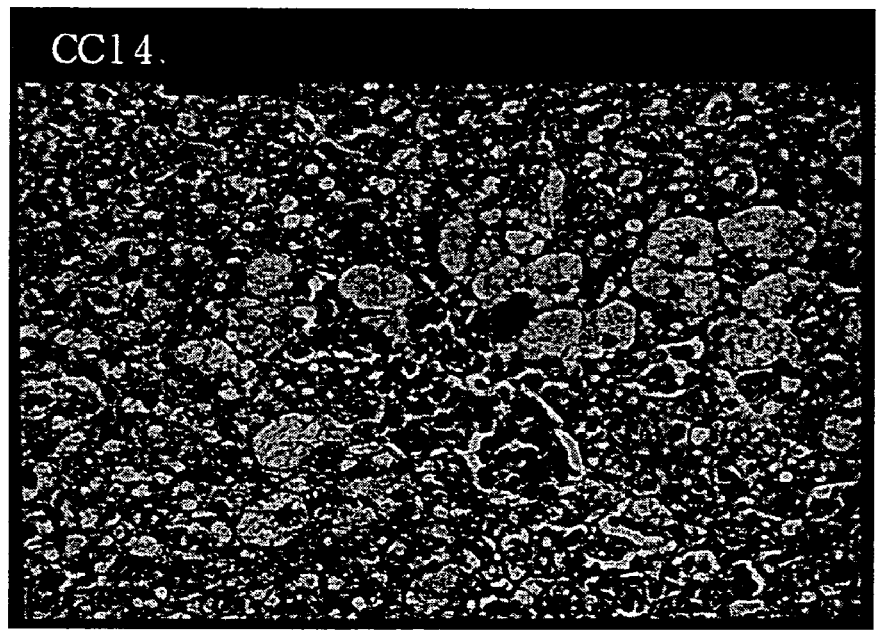
FIG. 3 is a biopsy of a $CCl_4$-induced acute hepatitis liver observed through an optical microscope.
Figure 4:
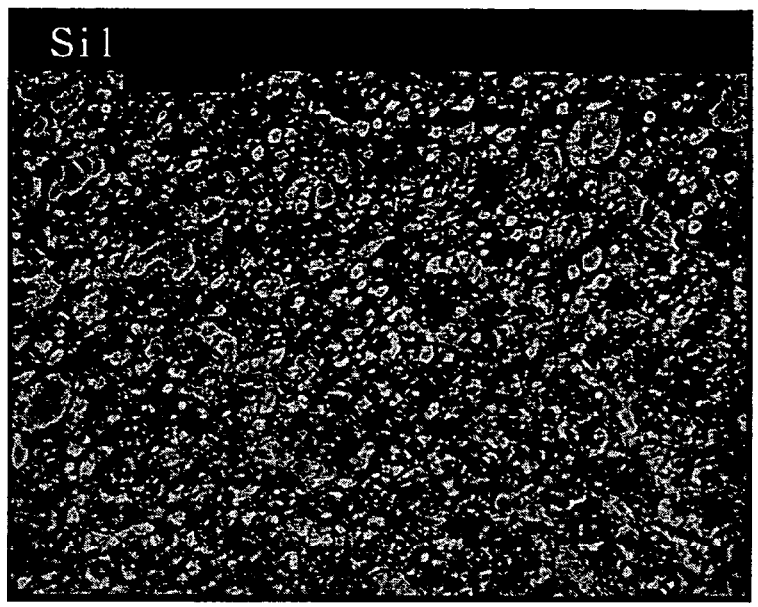
FIG. 4 is a biopsy of a liver with $CCl_4$-induced acute hepatitis and treated with silymarinobserved through an optical microscope.
Figure 5:
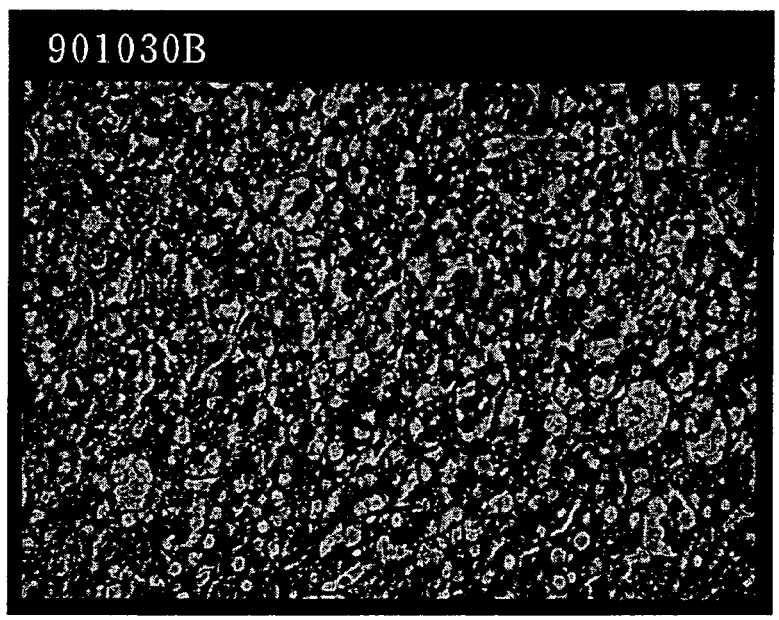
FIG. 5 is a biopsy of a liver with $CCl_4$-induced acute hepatitis and treated with ICH 16 observed through an optical microscope.

Embodiment 2
1. 8 kg of Artemisiae Capillaris, 6 kg of ground Gardenia Jasminoides and 144 kg of pure water are added together into a 250 ml decocting trough and mixed for 13 h.
2. Said mixture is extracted at 80° C. for 1 h, and cooled to 35° C. for further use.
3. 2 kg of ground Rheum Officinalis and 48 kg of 95% ethanol are added to the above-mentioned liquid decoction at 35° C. for 1 h. for extraction.
4. Said extraction of the liquid decoction is filtrated through a 200-mesh sieve to form 168.89 kg of liquid extract, containing 1.01 wt % solid measured by a moisture analyzer.
5. Said liquid extract is concentrated under reduced pressure by a vacuum concentrator to obtain 16.51 kg of liquid concentrate, containing 10.05 wt % solid measured by moisture analyzer.
6. Said liquid concentrate is put into a precipitating tank, and stirred by mechanical mixer. 62.3 kg of 95% ethanol is slowly added until the final concentration of the mixed liquid concentrate is about 80%. Then, the mixer is stopped and the concentrate is incubated for 1 h.
7. Said mixture is further filtrated by centrifugation using a centrifugal filtrator, the supernatant is kept and then the filtrate is collected and dried by a lyophilizer to obtain 182.26 g of product, which is coded as ICH16. An animal study was performed with said product, and the results are shown as Tables 1, 3 and FIG. 5.
8. Said supernatant produced in step 7 is further concentrated to a certain concentration, and dried in the lyophilizer to obtain 1105.6 g of product coded as ICH19-1. Another animal study was performed with said product, and the results are shown as Tables 1 and 3.

Embodiment 3
1. 8 kg of Artemisiae Capillaris, 6 kg of ground Gardenia Jasminoides and 144 kg of pure water are added together into a 250 ml decocting trough and mixed for 13 h.
2. Said mixture is extracted at 80° C. for 1 h and cooled to 35° C. for further use.
3. 2 kg of ground Rheum Officinalis and 48 kg of 95% ethanol are added to the above-mentioned liquid decoction for extraction at 35° C. for 1 h.
4. Said extraction of the liquid decoction is filtrated through a 200-mesh sieve to form 168.89 kg of first liquid extract, containing 1.01 wt % solid measured by a moisture analyzer.
5. Said first liquid extract is concentrated under a reduced pressure by a vacuum concentrator to obtain 16.51 kg of second liquid concentrate, containing 10.05 wt % solid measured by a moisture analyzer.
6. Said second liquid concentrate is put into a precipitating tank and stirred by a mechanical mixer. 15.58 kg of 95% ethanol is slowly added until the final concentration mixed liquid concentrate is about 50%. Then, the mixer is stopped and the mixture is incubated for 1 h.
7. Said mixture is further filtrated by centrifugation using a centrifugal filtrator, and then a third liquid filtrate is collected in a precipitating tank and stirred by a mechanical mixer. 46.73 kg of 95% ethanol is slowly added. Then, the mixer is stopped and the mixture is incubated for 1 h.

Figure 7:
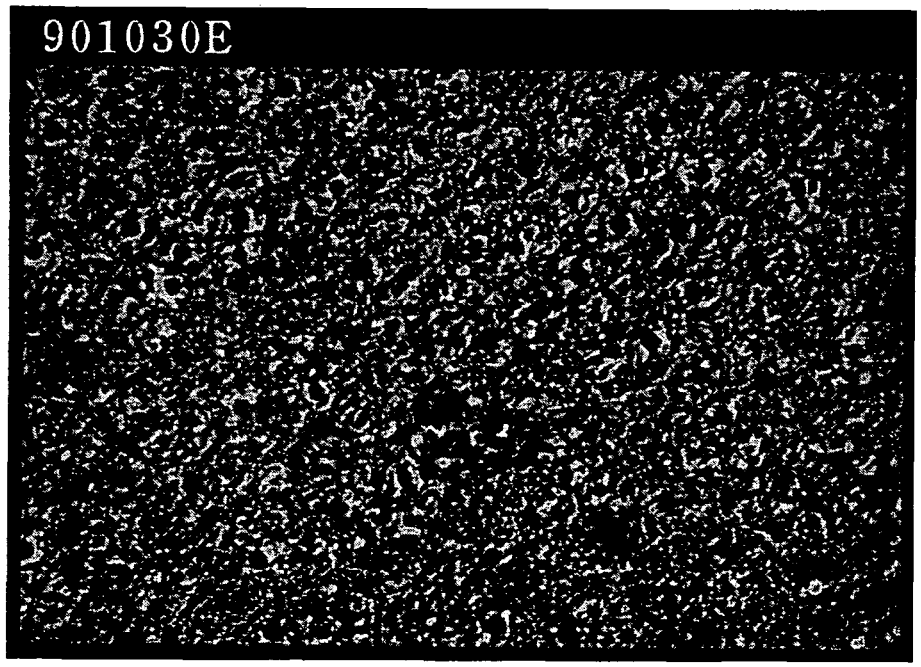
FIG. 7 is a biopsy of a liver with $CCl_4$-induced acute hepatitis and treated with ICH 20 observed through an optical microscope.

8. Said mixture is further filtrated by centrifugation using a centrifugal filtrator, the supernatant is kept, the filtrate is collected and dried by a lyophilizer to obtain 118.98 g product coded as ICH20. An animal study was performed with said product, and the results are shown as Tables 1, 3 and FIG. 7.

9. Said supernatant produced in step 8 is further concentrated to a certain concentration and dried in the lyophilizer to obtain 1102.7 g product coded as ICH19. Another animal study was performed with said product, and the results are shown as Table 1 and 3.

Embodiment 4 Traditional Water Extraction 1. 8 kg of Artemisiae Capillaris, 6 kg of ground Gardenia Jasminoides, 2 kg of Rheum Officinalis and 144 kg of pure water are added together into a 250 ml decocting trough, and mixed.

2. Said mixture is decocted at 100° C. for 1.5 to 2 h and cooled for further use.

3. Said liquid decoction is filtrated through a 200-mesh sieve to form 112.2 kg of liquid extract, containing 1.03 wt % solid measured by a moisture analyzer.

4. Said liquid extract is concentrated under reduced pressure by a vacuum concentrator to obtain 5.58 kg of liquid concentrate, containing 20.05 wt % solid measured by a moisture analyzer.

5. Said liquid concentrate is further dried in the lyophilizer to obtain 1118.79 g product coded as ICH. An animal study was performed with said product, and the results are shown as Tables 1 and 3.

B. Animal in Vivo Study

The extracts prepared from previous embodiments are treated in rats with liver damage induced by carbon tetrachloride ($CCl_4$), and serum GOT (Glutamyl Oxaloacetic Transaminase) and GPT (Glutamyl Pyrubic Transaminase) values of the rats were observed. The liver enzymes were dramatically released to the blood stream when the hepatocyte was damaged, and thus the serum GOT and GPT values increased. Hence, the extracts before and after treatment are compared together to see the GOT and GPT variations. In other words, the restoration effects of the extracts on the damaged liver were evaluated through comparing the GOT and GPT variations before and after a treatment of the extracts. Furthermore, the curing effects of the extracts on the swelling liver damaged by the chemicals were also evaluated through comparing their weight.

1. Acute Hepatitis Induced by $CCl_4$

The rats were randomly divided, with six rats in each group. In the study, control and toxicant groups were orally given distilled water, testing groups were orally given the products from different processes (ICH17, ICH16, ICH19, ICH19-1, and ICH20 with different doses which were diluted with maltodextrin until the amount is the same), the reference group was orally given silymarin (25 mg/kg in 1% CMC). One hour later, each group was i.p. with carbon tetrachloride ($CCl_4$; 1.5 ml/kg in olive oil, 20%), except the control group which was i.p. with olive oil. After 24 hours, the animals were anesthetized with ether, and the blood was collected from the carotid arteries. The serum was separated and incubated at room temperature for 10 minutes and then centrifuged (Backman centrifuge, GS-6R, 3000 rpm) for another 10 minutes. The activities of rat serum GOT (Glutamyl Oxaloacetic Transaminase) and GPT (Glutamyl Pyrubic Transaminase) were measured. The results are shown in the following table.

TABLE 1

The results of $CCl_4$-induced animal study

| | Dose (mg/kg) | GOT (U/L) | GPT (U/L) |
|---|---|---|---|
| Normal | — | 129.83 ± 7.03 | 49.37 ± 2.06 |
| $CCl_4$ | — | 648.1 ± 44.1 | 388.1 ± 35.5 |
| $CCl_4$ + Silymarin ™ | 25 | 263.7 ± 20.6 | 126.7 ± 18.4 |
| $CCl_4$ + ICH16 | 141.6$^a$ | 236.3 ± 27.5*** | 171.2 ± 42.9 |
| $CCl_4$ + ICH17 | 50.7$^a$ | 198.5 ± 27.6*** | 145.2 ± 17.1** |
| $CCl_4$ + ICH20 | 92.4$^a$ | 184.9 ± 22.3*** | 164.4 ± 21.3* |
| $CCl_4$ + ICH19 | 856.7$^a$ | 384.3 ± 27.2 | 412.8 ± 64.7 |
| $CCl_4$ + ICH19-1 | 858.9$^a$ | 400.8 ± 112.7 | 418.3 ± 54.8 |
| $CCl_4$ + ICH (Traditional Water Extraction) | 1000$^a$ | 426.5 ± 56.2** | 143 ± 26.6** |

(N = 6, *p < 0.05, p < 0.01, *p < 0.001 compared to the $CCl_4$ group, One Way ANOVA folled by Scheffe's test)
$^a$Due to the diversity of concentration process, the dose given in each group was different. However, the amount given in each group comes from the same amount of herbs.

Ref Recknagel R O. Carbon tetrachloride hepatotoxicity. [Review][351 refs], *Pharmacological Reviews.* 19(2): 145–208,1967

2. Preparation of Pathological Tissue Slice

After blood was collected, the liver of the carbon tetrachloride-induced acute hepatitis of the animal was separated, and liver tissue around 0.5 cm$^3$ in each folium was taken out. Those tissues were fixed in 10% neutral formalin for 1 to 2 weeks, then dehydrated and paraffin-embedded, and cut into 4 to 5 μm liver slices by a rotary microtome. The slices were stained with Haematoxylin and Eosin, and the pathological patterns were observed under an optical microscope. The results are shown as Table 2 and FIGS. 2 to 7.

TABLE 2

The Report of Tissue Biopsy

| Slice No. | Normal | $CCl_4$ | Silymarin | ICH16 | ICH20 | IHC17 |
|---|---|---|---|---|---|---|
| Tissue observations, liver | T | T | T | T | T | T |
| Fatty change, centrilobular | — | 2 | 1 | 1 | — | — |
| Vacuolar degeneration/ Swollen cells, diffuse | — | 2 | 2 | 1 | 1 | 1 |

Symbols illustration:
T: Tissue present; adequate for microscopic evaluation
Evaluation of the extent in tissue lesion:
—: No observation
1: Observed mineral tissue lesion
2: Observed mild tissue lesion
3: Observed moderate tissue lesion
4: Observed severe tissue lesion 3. D-Galactosamine-Induced Acute Hepatitis Five male rats were divided in each group, each rat with body weight about 200±20 g. In the study, control and toxicant groups were orally given with distilled water (0.9% NaCl) while testing groups were orally given the products from different processes (ICH17, ICH16, ICH19, ICH19-1, and ICH20 with different doses were diluted with maltodextrin until the amount is the same). The reference group was orally given guanine (300 mg/kg). Half an hour later, each group was i.p. with d-galactosamine (500 mg/kg), except the control group. Four and eight hours after first injection, test substances were administered orally again at the same dose. After 24 hours, the animals were sacrificed, and the blood was collected from the carotid arteries. The serum was separated and incubated at room temperature for 10 minutes, and then centrifuged (Backman centrifuge, GS-6R, 3000 rpm) for another 10 minutes. The activities of rat serum GOT (Glutamyl Oxaloacetic Transaminase) and GPT (Glutamyl Pyrubic Transaminase) were measured. The results are shown in Table 3.

TABLE 3

The results of d-galactoamine-induced acute hepatitis animal study

| | Dose (mg/kg) | GOT (U/L) | GPT (U/L) |
|---|---|---|---|
| Normal | — | 126.4 ± 4.4 | 64.4 ± 3.7 |
| d-gal | — | 1778.4 ± 87.5 | 1035.6 ± 95.2 |
| d-gal + Guanine | 300 × 3 | 1024.8 ± 91.1* | 602.4 ± 61.7 |
| d-gal + ICH16 | 141.6$^a$ × 3 | 1498.0 ± 168.6* | 753.6 ± 46.3* |
| d-gal + ICH17 | 50.7$^a$ × 3 | 1406.4 ± 156.9* | 890.4 ± 83.7* |
| d-gal + ICH20 | 92.4$^a$ × 3 | 987.6 ± 133.7** | 522.8 ± 73.2*** |
| d-gal + ICH19 | 856.7$^a$ × 3 | 2151.4 ± 189.4 | 1304.9 ± 124.5 |
| d-gal + ICH19-1 | 858.9$^a$ × 3 | 1926.0 ± 169.4 | 1399.0 ± 144.5 |
| d-gal + ICH (Traditional Water Extraction) | 1000$^a$ × 3 | 1462.0 ± 337.5* | 817.6 ± 111.2* |

(N = 5, *$p < 0.05$, $p < 0.01$, *$p < 0.001$ compared to the d-gal group, One Way ANOVA followed by Scheffe's test)
$^a$Due to the diversity of concentration process, the dose given in each group is different. However, the amount given in each group comes from the same amount of herbs.

Ref: Keepler, D., Lesch, R., Reutler, W. and Decher, K. Experimental Hepatitis induced by D-galactosamine. *Experiment and Molecular Patholody* 9, 279–290, 1968

From the above results, it is shown that the extracts prepared from the present invention could reduce the high rat serum GOT and GPT values induced by $CCl_4$ and d-galactosamine. More particularly, comparing to the reference groups (silymarin and guanine), toxicant groups ($CCl_4$ and d-galactosamine) and the traditional water extraction (ICH), the ICH16, ICH17 and ICH20 prepared by the present process could obviously lower the high rat serum s-GOT and s-GPT values induced by $CCl_4$ and d-galactosamine in the animal study. In addition, comparing to the reference group (silymarin) and the toxicant group ($CCl_4$), the ICH16, ICH17 and ICH20 prepared by the present process could also reduce the fatty change of centrilobular, the diffused vacuolar degradation and swollen cells induced by $CCl_4$. That is, the extracts prepared by the present invention could highly protect or repair the damaged liver.

According to the process in the present invention, active components thus obtained are effectively extracted, purified and concentrated. The high concentration ratio by the process of the present invention is illustrated in Table 4.

TABLE 4

The relationship between the present invention and the traditional process in a concentration ratio

| | Herbs usage (kg)$^a$ | Final production (g) | Concentration ratio | Animal dosage (mg/kg) | Animal dosage ratio |
|---|---|---|---|---|---|
| Traditional process | 16 | 1119 | 1 | 1000 | 1 |
| (ICH17) | 16 | 65.26 | 17.1 | 50.7 | 0.05 |
| (ICH20) | 16 | 118.98 | 9.4 | 92.4 | 0.09 |
| (ICH16) | 16 | 182.26 | 6.1 | 141.6 | 0.14 |

$^a$16 kg of herbs comprising 8 kg of Artemisiae Capillaris, 6 kg of grounded Gardenia Jasminoides and 2 kg of Rheum Officinalis.

From Table 4, it is shown that herbs with the same weight (16 kg) are utilized initially, the final products in traditional process are 1119 g, and with the purification and concentration steps in the present invention, the final products are 65.26 g, 118.98 g and 182.26 g in different processes. Furthermore, from the data in Table 4, comparing to the traditional process, the present process could further promote the concentration ratio to 17.1–6.1 folds. Thus, for the animal experiment, the dosage from the present process is as low as 0.05 to 0.14 folds more than the traditional process, and the effect is better than the traditional dosage, even the reference dosage. Therefore, it is shown that the process by the present invention could extract the entire effective components and effectively lower the dosage in the comparison with traditional process.

Besides, it is found that the active components in Rheum Officinalis are easily destroyed by heat, thus particularly, said material is extracted by alcohol at low temperature to release said active components rather than water decoction. Further, due to the sensitivity of temperature, Rheum Officinalis is separated and added after decoction and cooling of others, to reduce the destruction of active components by high temperature. In the present invention, the purification process removes the unnecessary substances and obtains the highly concentrated effective components. From the above, it is known that the present invention overcomes the failures of the traditional decoction method, and thus the effective components are largely extracted and completely conserved with separation and purification art. Therefore, the process in the present invention is novel and efficacious.

In addition, the extraction step in the present invention uses 'medicinal degree' alcohol and water rather than toxic organic solvents, so it is not harmful to a human body. Persons skilled in this art can realize that the alcohol-only extraction 'could hardly reach an optimal potency. However, with further studies and several experiments the exact range of alcohol concentrations is obtained for the optimum production of efficacious components. Furthermore, it is found that the products doubly precipitated by alcohol have high percentage of efficacious components and excellent results in animal studies. Moreover, it is also found that the solid weight percentage of the concentrate is very important to the ratio of efficacious components in the concentration step. This observation has not been disclosed in the prior art.

Although the present invention has been explained in relation to its preferred embodiment, it is to be understood that many other possible modifications and variations can be made without departing from the spirit and scope of the invention as hereinafter claimed.

What is claimed is:

1. A composition for treating a diseased human liver, prepared by the following steps comprising:
   (a) grinding Artemisiae Capillaris and Gardeniae Fructus, mixing them with pure water, and heating the mixture achieved from the grinding and mixing of Artemisiae Capillaris and Gardeniae Fructus;
   (b) adding a Rhei Rhizoma herb and alcohol into said mixture, and extracting to form a first solid phase and a first liquid phase;
   (c) concentrating said first liquid phase to form a concentrate; and
   (d) adding alcohol into said concentrate for precipitation and forming a second solid phase and a second liquid phase; separating said second solid phase from said second liquid phase and drying said second solid phase to form said composition for treatment of a human liver disease;

wherein said Artemisiae Capillaris is selected from the group consisting of Artemisiae Capillaris, Artemisiae scopariae and Herba Artemisiae annuae; wherein said Gardeniae is selected from the group consisting of Gardenia jasminoides and Gardenia radicans; and wherein said Rhei rhizoma is selected from the group consisting of Rheum officinalis and Rhubarb Shui-Ken.

2. The composition as claimed in claim 1, further comprising adding a Schizandrae Fructus herb and alcohol in step (b).

3. The composition as claimed in claim 1, wherein the concentration step in step (c) is achieved by concentrating said first liquid phase to form a concentrate containing 1 to 30 wt % solid.

4. The composition as claimed in claim 1, wherein a final concentration of alcohol in step (d) is 71 to 90 wt %.

5. The composition as claimed in claim 1, wherein a final concentration of alcohol in step (d) is 30 to 70 wt %.

6. The composition as claimed in claim 1, wherein the Artemisiae Capillaris is Artemisiae Capillaris.

7. The composition as claimed in claim 1, wherein the Gardeniae Fructus is Gardenia Jasminoides.

8. The composition as claimed in claim 1, wherein the Rhei Rhizoma is Rheum Officinalis.

9. The composition as claimed in claim 1, wherein step (a) further comprises boiling and stirring.

10. The composition as claimed in claim 1, the heated mixture in step (a) is cooled to 10 to 80° C.

11. The composition as claimed in claim 1, wherein the step (b) is performed by extracting said mixture at 10 to 80° C.

12. The composition as claimed in claim 1, wherein the weight ratio of Artemisiae Capillaris to Gardeniae Fructus to Rhei Rhizoma is 4:8 to 3:6 to 0.5:2.5.

13. The composition as claimed in claim 1, wherein the drying step in step (d) is performed by lyophilizing, spray drying or fluidized bed drying method.

14. A process for preparing a composition used for treatment of a human liver disease, comprising the following steps:
  (a) grinding Artemisiae Capillaris and Gardeniae Fructus, mixing them with pure water, and heating a mixture achieved from the grinding and mixing of Artemisiae Capillaris and Gardeniae Fructus;
  (b) adding a Rhei Rhizoma herb and alcohol into said mixture, and extracting to form a first solid phase and a first liquid phase;
  (c) concentrating said first liquid phase to form a concentrate; and
  (d) adding alcohol into said concentrate for precipitation and forming a second solid phase and a second liquid phase; separating said second solid phase from said second liquid phase and drying said second solid phase to form said composition for treatment of a human liver disease;
  wherein said Artemisiae is selected from the group consisting of Artemisiae Capillaris, Artemisiae Scopariae Herba and Herba Artemisiae annuae; said Gardeniae is selected from the group consisting of Gardenia jasminoides and Gardenia radicans; and wherein said Rhei rhizoma is selected from the group consisting of Rheum officinalis and Rhubarb Shui-Ken.

15. The process as claimed in claim 14, further comprising adding a Schizandrae Fructus herb and alcohol in step (b).

16. The process as claimed in claim 14, wherein the concentration step in step (c) is achieved by concentrating said first liquid phase to form a concentrate containing 1 to 30 wt % solid.

17. The process as claimed in claim 14, wherein a final concentration of alcohol in step (d) is 71 to 90 wt %.

18. The process as claimed in claim 14, wherein a final concentration of alcohol in step (d) is 30 to 70 wt %.

19. The process as claimed in claim 14, wherein the Artemisiae Capillaris is Artemisiae Capillaris.

20. The process as claimed in claim 14, wherein the Gardeniae Fructus is Gardenia Jasminoides.

21. The process as claimed in claim 14, wherein the Rhei Rhizoma is Rheum Officinalis.

22. The process as claimed in claim 14, wherein step (a) further comprises boiling and stirring.

23. The process as claimed in claim 1, the heated mixture in step (a) is cooled to 10 to 80° C.

24. The process as claimed in claim 14, wherein the step (b) is performed by extracting said mixture at 10 to 80° C.

25. The process as claimed in claim 14, wherein the drying step in step (d) is performed by lyophilizing, spray drying or fluidized bed drying method.

26. The process as claimed in claim 14, wherein the weight ratio of Artemisiae Capillaris to Gardeniae Fructus to Rhei Rhizoma is 4:8 to 3:6 to 0.5:2.5.

27. The process as claimed in claim 14, further comprising grinding, granulating, and packaging the composition as a capsule.

28. A composition for treating a diseased human liver, prepared by the following steps comprising:
  (a) grinding Artemisiae Capillaris and Gardeniae Fructus, mixing them with pure water, and heating the mixture achieved from the grinding and mixing of Artemisiae Capillaris and Gardeniae Fructus;
  (b) adding a Rhei Rhizoma herb and alcohol into said mixture, and extracting to form a first solid phase and a first liquid phase;
  (c) concentrating said first liquid phase to form a concentrate; and
  (d) adding alcohol into said concentrate for precipitation and forming a second solid phase and a second liquid phase; separating said second solid phase from said second liquid phase and drying said second solid phase;
  (e) adding alcohol into said second liquid phase for precipitation and forming a third solid phase and a third liquid phase until a final concentration of alcohol is 75 to 90 wt % separating said third solid phase from said third liquid phase and then drying said third solid phase to form said composition for the treatment of a human liver disease; and
  wherein said Artemisiae Capillaris is selected from the group consisting of Artemisiae Capillaris, Artemisiae scopariae and Herba Artemisiae annuae; wherein said Gardeniae is selected from the group consisting of Gardenia jasminoides and Gardenia radicans; and wherein said Rhei rhizoma is selected from the group consisting of Rheum officinalis and Rhubarb Shui-Ken.

29. A process for preparing a composition used for treatment of a human liver disease, comprising the following steps:
  (a) grinding Artemisiae Capillaris and Gardeniae Fructus, mixing them with pure water, and heating a mixture achieved from the grinding and mixing of Artemisiae Capillaris and Gardeniae Fructus;

(b) adding a Rhei Rhizoma herb and alcohol into said mixture, and extracting to form a first solid phase and a first liquid phase;
(c) concentrating said first liquid phase to form a concentrate; and
(d) adding alcohol into said concentrate for precipitation and forming a second solid phase and a second liquid phase; separating said second solid phase from said second liquid phase having a final concentration of alcohol of 30–70 wt % and drying said second solid phase;
(e) adding alcohol into said second liquid phase for precipitation and forming a third solid phase and a third liquid phase until a final concentration of alcohol is 75 to 90 wt %; separating said third solid phase from said third liquid phase and then drying said third solid phase to form said composition for the treatment of a human liver disease; and wherein said Artemisiae is selected from the group consisting of Artemisiae Capillaris, Artemisiae Scopariae Herba and Herba Artemisiae annuae; said Gardeniae is selected from the group consisting of Gardenia jasminoides and Gardenia radicans; and wherein said Rhei rhizoma is selected from the group consisting of Rheum officinalis and Rhubarb Shui-Ken.

* * * * *